US012797053B2

(12) United States Patent
Truckai

(10) Patent No.: US 12,797,053 B2
(45) Date of Patent: Nov. 17, 2026

(54) ELECTROSURGICAL DEVICE AND METHOD OF USE

(71) Applicant: Meditrina, Inc., San Jose, CA (US)

(72) Inventor: Csaba Truckai, San Jose, CA (US)

(73) Assignee: Meditrina, Inc., San Jose, CA (US)

( * ) Notice: Subject to any disclaimer, the term of this patent is extended or adjusted under 35 U.S.C. 154(b) by 107 days.

(21) Appl. No.: 18/951,336

(22) Filed: Nov. 18, 2024

(65) Prior Publication Data

US 2025/0160804 A1 May 22, 2025

Related U.S. Application Data

(60) Provisional application No. 63/601,651, filed on Nov. 21, 2023.

(51) Int. Cl.

| | |
|---|---|
| ***A61B 10/02*** | (2006.01) |
| ***A61B 17/32*** | (2006.01) |
| ***A61B 17/3205*** | (2006.01) |
| ***A61B 18/00*** | (2006.01) |
| ***A61B 18/14*** | (2006.01) |

(52) U.S. Cl.

CPC ...... *A61B 10/0266* (2013.01); *A61B 18/1402* (2013.01); *A61B 2017/320064* (2013.01); *A61B 17/32053* (2013.01); *A61B 2018/00208* (2013.01); *A61B 2018/00601* (2013.01); *A61B 2218/007* (2013.01)

(58) Field of Classification Search

CPC ............ A61B 10/0266; A61B 18/1402; A61B 17/32053; A61B 2017/320064; A61B 2018/00208; A61B 2018/00601; A61B 2218/007

USPC .......................................................... 600/566

See application file for complete search history.

(56) References Cited

U.S. PATENT DOCUMENTS

| | | | | |
|---|---|---|---|---|
| 6,007,512 A * | 12/1999 | Hooven | A61B 17/32002 | 606/45 |
| 2015/0057658 A1* | 2/2015 | Sutton | A61B 18/148 | 606/41 |
| 2023/0040816 A1* | 2/2023 | Cheng | A61B 18/1206 | |

* cited by examiner

*Primary Examiner* — Mark Edwards

(74) *Attorney, Agent, or Firm* — Levine Bagade Han LLP

(57) ABSTRACT

Bipolar electrosurgical devices and methods of use for cutting tissue and extracting tissue cores for biopsy and other purposes.

26 Claims, 11 Drawing Sheets

ELECTROSURGICAL DEVICE AND METHOD OF USE

CROSS-REFERENCE TO RELATED APPLICATIONS

This application is a non-provisional of U.S. Provisional application No. 63/601,651 filed Nov. 21, 2023, the entirety of which is incorporated by reference.

FIELD OF THE INVENTION

The present invention relates to bipolar electrosurgical devices and methods of use for cutting tissue and extracting tissue cores for biopsy and other purposes.

SUMMARY OF THE INVENTION

The present disclosure relates to bipolar electrosurgical devices and methods of using bipolar electrosurgical devices. Such devices can comprise a handle and an elongated shaft coupled to the handle with a motor drive and drive mechanism adapted to helically advance an RF cutting sleeve into targeted tissue to cut a tissue core. The cutting sleeve can be rotated without helical advancement wherein a projecting element of the electrode excises the distal end of the tissue core and captures the tissue core in a lumen of the cutting sleeve.

Variations of the present disclosure include methods of obtaining a tissue core for biopsies. For example, such methods can include providing an elongate cutting member having a longitudinal passageway extending about a central axis to a distal end carrying a RF electrode, wherein at least a portion of the RF electrode extends from an outer periphery of the elongate cutting member to the central axis; and actuating the RF electrode; helically advancing the elongate cutting member into a targeted tissue region wherein the RF electrode cuts tissue to thereby capture a tissue core in the longitudinal passageway; rotating the elongate cutting member without helical advancement thereby causing the RF electrode to cut a distal end of the tissue core captured in the longitudinal passageway; and withdrawing the elongate cutting member from the targeted tissue region thereby obtaining an extracted tissue core.

Variations methods can include actuating the RF electrode contemporaneous with helically advancing the elongate cutting member into the targeted tissue region. In some cases, helically advancing and rotating the elongate cutting member are accomplished with a drive mechanism in a handle coupled to the elongate cutting member. The drive mechanism can include a motor drive or a manually actuated mechanism.

Variations of the methods include helically advancing the elongate cutting member using a first drive mechanism and rotating the elongate cutting member is accomplished with a second different drive mechanism. The elongate cutting member can be helically advanced from an outer sleeve coupled to the handle.

Variations method can further include stabilizing the targeted tissue region contemporaneous with helically advancing the elongate cutting member. For example, stabilizing can be accomplished by at least one of coupling the distal end of the outer sleeve with a surface of the tissue with negative pressure in the outer sleeve or grasping the surface of the targeted tissue region with a grasping device.

In additional variations the distal end of the elongate cutting member is configured with a helical element that helically drives the elongate cutting member into tissue which stabilizes the targeted tissue region.

Variations of the present disclosure methods of obtaining multiple tissue cores by repeating actuating, helically advancing and rotating the elongate cutting member to obtain each additional tissue core.

The present disclosure also includes electrosurgical tissue cutting devices for obtaining a tissue core for biopsy. For example, such devices can include a handle coupled to an elongate shaft assembly extending about a central axis and including an outer sleeve and an inner cutting sleeve coaxial to the outer sleeve and with a longitudinal passageway therein for capturing tissue; an RF electrode carried at a distal end of the inner cutting sleeve, wherein an extending element of the RF electrode extends from an outer periphery of the inner cutting sleeve to the central axis; and at least one selectable drive mechanism in the handle for (i) helically advancing the inner cutting sleeve distally from the outer sleeve, and for (ii) rotating the inner cutting sleeve in the outer sleeve without helical advancement.

The electrosurgical tissue cutting device can further include a negative pressure source coupled to the elongate shaft assembly. In some variations, the negative pressure source communicates with an annular passageway in the outer sleeve outward of the inner cutting sleeve for stabilizing targeted tissue region. In additional variations the negative pressure source communicates with the longitudinal passageway in the inner cutting sleeve for aspirating cut tissue therein.

The devices can include a drive mechanism comprising a motor drive or a manually actuated mechanism.

Variations of the present disclosure include an electrosurgical tissue cutting device using an RF source coupled to the RF electrode and a controller adapted to control the RF source, the negative pressure source and at least one selectable drive mechanism.

Variations of the present disclosure include an electrosurgical tissue cutting device further including a detachable coupling between the handle and the elongate shaft assembly for detaching at least a portion of the elongate shaft assembly for retrieval of tissue cores from the inner cutting sleeve.

Variations of the present device can include a distal edge of the inner cutting sleeve around the longitudinal passageway includes an RF electrode.

In additional variations the extending element of the RF electrode that extends from the outer periphery of the inner cutting sleeve toward the central axis has a non-helical configuration. The extending element of the RF electrode can extend from the outer periphery of the inner cutting sleeve toward the central axis has a helical configuration.

Variations of the electrosurgical tissue cutting device can include an extending element of the RF electrode that extends from the outer periphery of the inner cutting sleeve toward the central axis is extendable and retractable.

DETAILED DESCRIPTION

Figure 1:
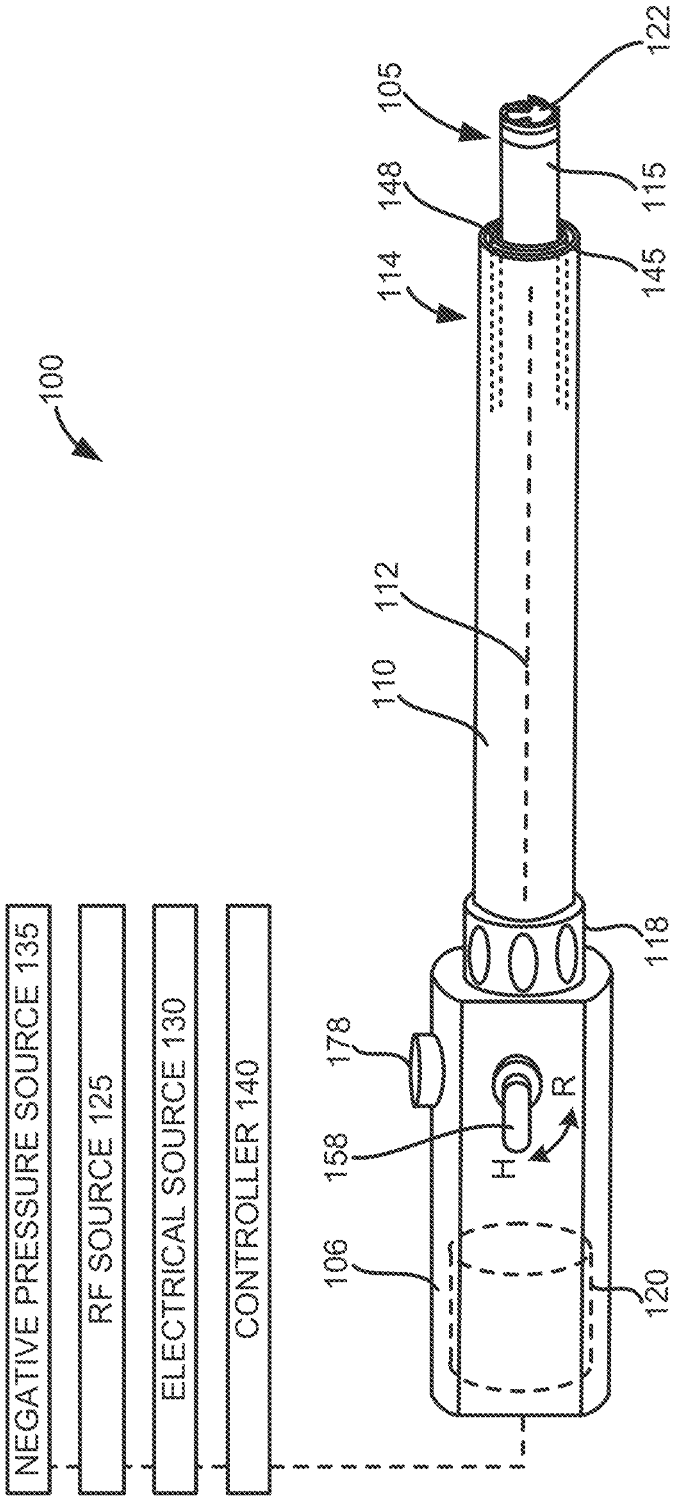
FIG. 1 is a side view of an RF device corresponding to the invention that has a handle connected to an elongate shaft assembly with a helically extendable-retractable cutting sleeve carrying an electrode arrangement for electrosurgically cutting at least one tissue core and capturing the tissue core in a lumen of the cutting sleeve, together with a block diagram of a negative pressure source, electrical source, RF source, and controller operatively coupled to the device.
Figure 2:
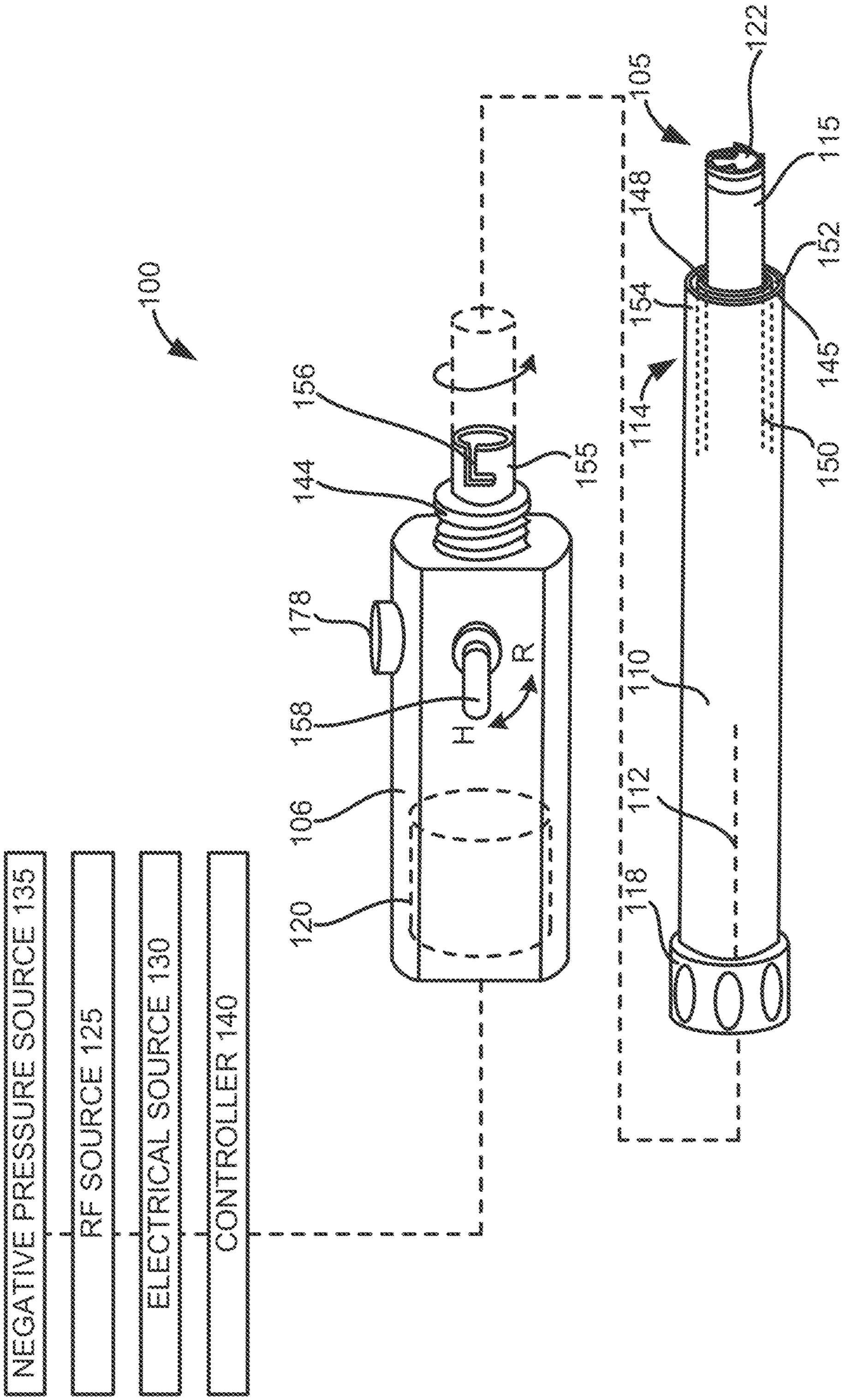
FIG. 2 is a side view of the RF device of FIG. 1 with the handle de-coupled from the elongate shaft assembly.
Figure 3A:
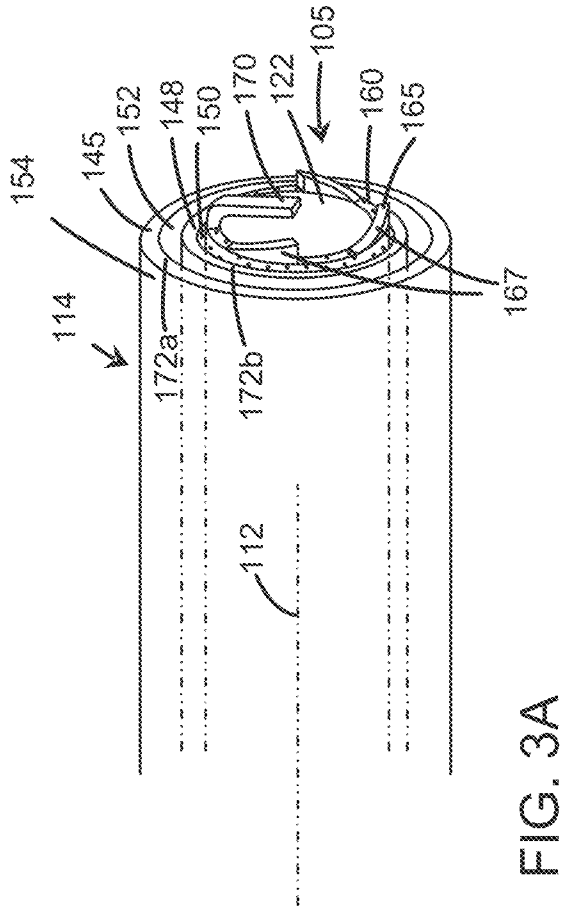
FIG. 3A is an angled view of the working end of the RF device of FIG. 1, showing the cutting sleeve in a retracted position in a guide sleeve of an outer sleeve assembly.
Figure 3B:
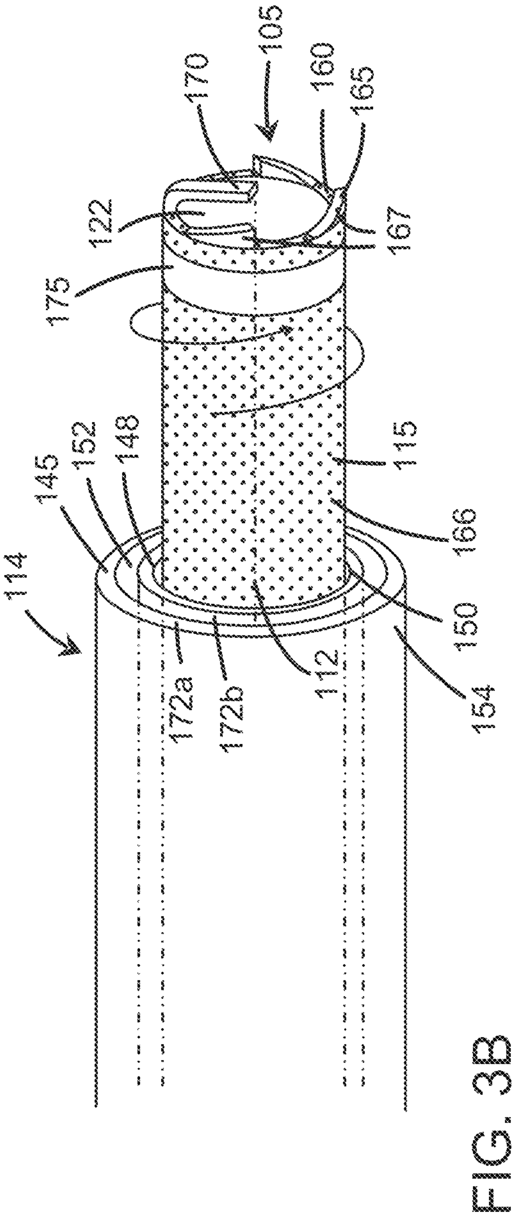
FIG. 3B is an angled view of the working end of FIG. 3A showing the cutting sleeve in a helically extended position distally outward from the guide sleeve.

FIGS. 1 and 2 illustrate an electrosurgical tissue cutting device 100, which may be monopolar or bipolar, or combination thereof but typically has a bipolar RF electrode arrangement 105 as depicted in the variation of FIGS. 3A-3B. The cutting device 100 comprises a handle 106 coupled to an elongated shaft 110 extending about central axis 112 and having a diameter of 2 mm to 15 mm. In a variation, the shaft 110 comprises an introducer sleeve assembly 114 and a co-axial inner cutting sleeve 115 that carries the bi-polar electrode arrangement 105. As can be seen in FIGS. 1 and 2, the shaft 105 has a hub 118 and typically is detachable from the handle 106. In a variation, the elongated shaft 110 is a single-use disposable component, and the handle 106 comprises a reusable component. FIG. 1 illustrates a motor drive 120 carried in the handle 106 that is coupled to a drive mechanism therein that can helically advance the cutting sleeve 115 or rotate the cutting sleeve 115 without helical movement as will be described further below. The cutting sleeve 115 has a lumen or passageway 122 extending about central axis 112 for receiving an excised tissue core, as will be described below.

In the variation of FIG. 1, the RF cutting device 100 is operatively connected to a remote RF source 125, an electrical source 130 for energizing the motor drive 120, a negative pressure source 135, and a controller 140, which is adapted to control the operating parameters of the RF source 125, the motor drive 120 and the negative pressure source 135.

Referring to FIGS. 1 and 2, it can be seen that the introducer sleeve assembly 114 of shaft 110 has a proximal hub 118 that can be locked onto a cooperating connector 144 in handle 106. The hub 118 and connector 144 (FIG. 2) can comprise a threaded fitting, a J-lock, or any other means for detachable connection of the components. The introducer sleeve assembly 114 comprises an outer sleeve 145 and an inner guide sleeve 148 with a central bore 150 in which the cutting sleeve 115 is extendable and retractable (FIG. 3A). As can be seen in FIGS. 1 and 3A-3B, the annular space 152 or passageway between the outer sleeve 145 and the guide sleeve 148 communicates with the negative source 135. The annular space 152 can have a suitable radial dimension to provide negative pressure adapted to suction a tissue surface against the distal end 154 of the introducer sleeve assembly 114 to stabilize targeted tissue T, as will be shown in FIGS. 4A to 4D below. Typically, the radial dimension of the annular space 152 can range from 1 mm to 5 mm.

From FIG. 2, it can also be understood that the cutting sleeve 115 is adapted for coupling to a drive member 155 in the handle 106. In FIG. 2, the drive member 155 has a distal end with J-lock fitting 156 for detachable connection to the proximal end of the cutting sleeve 115, which is out of view in FIG. 2. The drive member 155 is operatively coupled to the motor drive 120 and drive mechanism and is configured to selectively move in two ways: (i) helically outward and inward from the handle 106 to helically advance the cutting sleeve 115 in targeted tissue; and (ii) rotationally without helical movement to thereby rotate the cutting sleeve 115 at least 360°. In the variation shown in FIGS. 1 and 2, the handle carries a manual switch 158 for selecting either (i) helical movement of the cutting sleeve indicated at H or (ii) rotation only of the cutting sleeve 115 indicated at R. The handle 106 carries a drive mechanism (not shown) for converting rotation of the shaft of motor drive 120 to helical movement of the drive sleeve 115 as known in the art, such as a motor shaft that drives a pin in an arcuate slot in a cooperating drive sleeve. In a variation, a first drive component helically advances the drive member 155 and cutting sleeve 115 to an extended position and then helically retracts the drive member 155 and cutting sleeve 115 back to a retracted position as in FIG. 4A. A second drive component is adapted to rotate the drive member 155 at least 360° at any point in the helical stroke of the cutting sleeve 115, and typically at the end of the stroke. The switch 158 allows selection of either helical or rotational movement of the drive sleeve 155 while locking out the non-selected movement.

Now, turning to FIGS. 3A and 3B, the electrode arrangement 105 can be described in more detail. In FIG. 3B, it can be seen that a distal peripheral edge 160 of the cutting sleeve 115 comprises an active electrode 165. In a variation, the active electrode has a plurality of distally projecting edges or teeth 167 that can assist in electrosurgical cutting as the sleeve 115 is advanced helically in tissue. In various configurations, the peripheral edge 160 and active electrode 165 of the cutting sleeve 115 can be configured with serrations, teeth, or otherwise be smooth. The sleeve 115 may comprise a thin-wall metal tube with a sleeve portion proximal to active electrode 165 that has an electrically insulative coating 166 such that the uncoated portions form the active electrode 165 (see e.g., FIG. 3B). Such a thin layer of an insulative coating 166 can comprise any suitable thin heat shrink material such as a bio-compatible PFA, TEFLON®, polytetrafluoroethylene (PTFE), FEP (Fluorinated ethylene-propylene), polyethylene, polyamide, ECTFE (Ethylenechlorotrifluoro-ethylene), ETFE, PVDF, polyvinyl chloride or silicone. In another variation, the sleeve 115 can comprise a non-conductive material such as a polymeric or composite material. By covering substantial portions of the cutting sleeve 115 with an insulative layer 166, the total surface area of the active electrode 165 is minimized, which is advantageous.

FIGS. 3A and 3B further show that the active electrode 165 includes a projecting electrode element 170 that projects radially inward from the peripheral edge 160 and extends to, or slightly across, the central axis 112 of the lumen 122 of the cutting sleeve 115. Thus, it can be understood that helical rotation of the cutting sleeve 115 will cause the projecting active electrode element 170 to electrosurgically cut a spiral path through targeted tissue as the cutting sleeve 115 is advanced helically in tissue. In the variation of FIGS. 3A and 3B, the bi-polar electrode arrangement 105 is configured with the return electrode comprising at least a portion of the distal end 154 of the introducer sleeve assembly 114, which consists of the distal tip 172*a* of outer sleeve 145 and distal tip 172*b* of guide sleeve 148. Further, the return electrode 175 includes an annular band around an insulated portion of the cutting sleeve 115. As another alternative, an interior wall of lumen 122 of the cutting sleeve can comprise a return electrode. A ground pad (not shown) also can be provided. In using the device in a non-fluid (saline) immersed procedure, as will be described in FIGS. 4A-4D, it should be appreciated that the initial contact of the distal tips 172*a*, 172*b* of the outer sleeve 145 and guide sleeve 148 will provide a return electrode with a limited surface area. For this reason, as soon as the cutting sleeve 115 is advanced in tissue, the return electrode 175 or electrodes on the cutting sleeve 115 will increase the total surface area of the return electrode to thereby prevent heating of the return electrode.

FIGS. 1 and 2 also show that the handle 106 carries an actuator button 178 for actuating the RF source 125 to energize the electrode arrangement 105. In a variation, depressing button 178 contemporaneously (i) activates the negative pressure source 135, (ii) energizes the RF electrode arrangement 105, and (ii) activates the motor drive 120 to helically advance the cutting sleeve 115. The steps of a method of using the device 100 are illustrated in FIGS. 4A-4D below. In another variation, partly depressing button 178 would activate the negative pressure source 135 to allow the operator to suction tissue against the distal end 154 of the introducer sleeve assembly 114, after which further depressing of button 178 activates the RF electrode arrangement and activates the motor drive 120 to helically advance the cutting sleeve 115. In another variation, the controller 140 controls multiple functions, such as when the operator fully depresses button 178, the controller 140 (*i*) activates the RF electrode arrangement 105 and almost contemporaneously helically advances the cutting sleeve 115 through its helical stroke capturing a tissue core in lumen 122 of cutting sleeve 115, (ii) at the end of the stroke, then automatically rotates the cutting sleeve 360° to resect the distal end of the core of tissue; and (iii) then automatically retracts the cutting sleeve 115 either helically or axially after the 360° rotation of the cutting sleeve. As can be understood from FIGS. 3A and 4A, the negative pressure source 135 can be configured to communicate with lumen 122 of cutting sleeve 115, as well as the annular space 152 around the guide sleeve 148. Thus, negative pressure in the lumen 122 can assist in pulling the tissue core C (FIG. 4B) into the lumen 122 as the cutting sleeve is helically advanced into tissue. The controller 140 may further control a pressure control subassembly for providing different negative pressures in the lumen 122 and the annular space 152, for example, a greater suctioning pressure in the lumen 122 to extract tissue cores in the proximal direction.

Figure 4B:
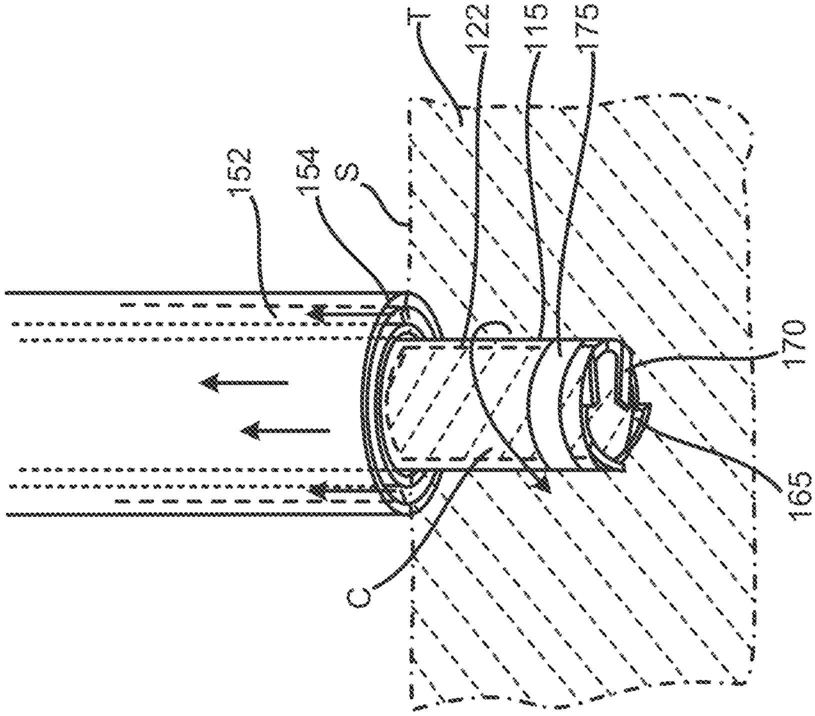
FIG. 4B is a schematic view of a subsequent step of the method of use wherein the electrode assembly is energized and the distal portion of the cutting sleeve is driven by a motor to cut into the target tissue capturing a tissue core in a lumen of the cutting sleeve.
Figure 4A:
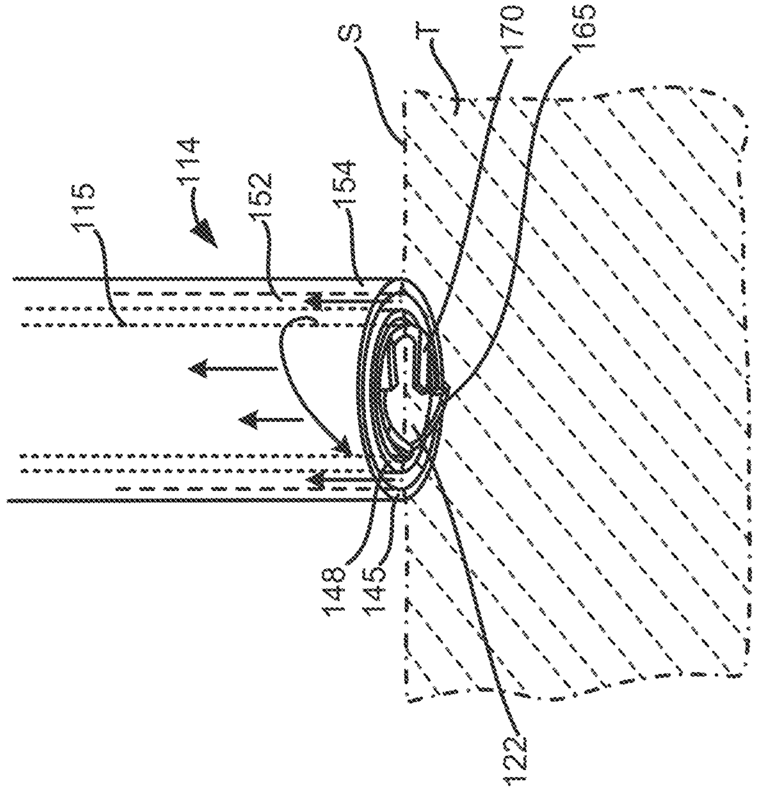
FIG. 4A is a schematic view of an initial step of a method of the invention wherein a distal end of the outer sleeve assembly is pressed against targeted tissue, and the negative pressure source is activated to suction the tissue into stabilizing contact with the distal tip of the outer sleeve assembly.
Figure 4C:
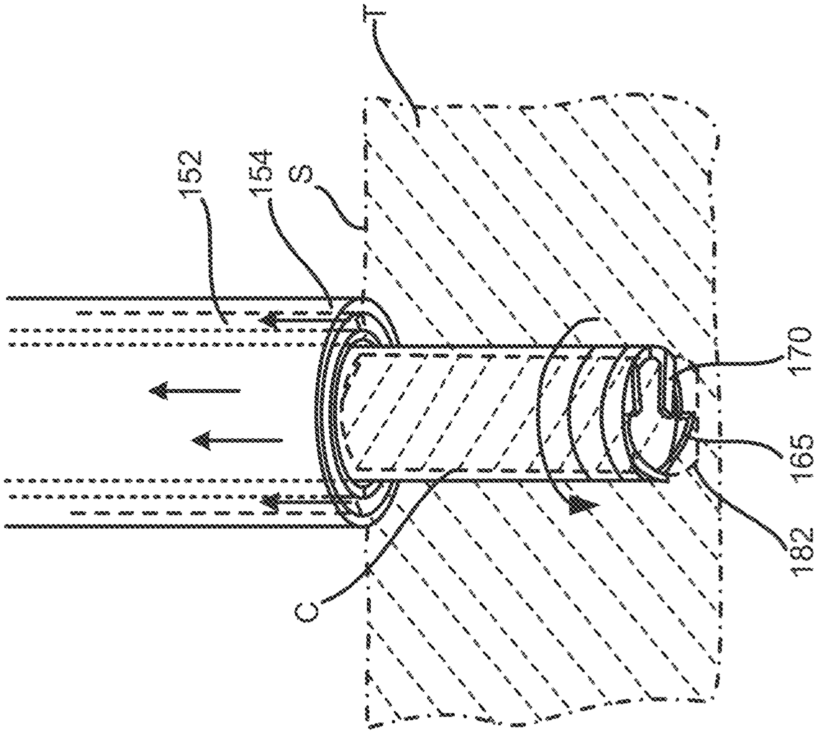
FIG. 4C is a schematic view of another step of the method of use wherein the cutting sleeve is rotated 360° or more without helical movement to thereby electrosurgically cut or excise a distal end of the tissue core and capture the tissue core in a lumen of the cutting sleeve.
Figure 4D:
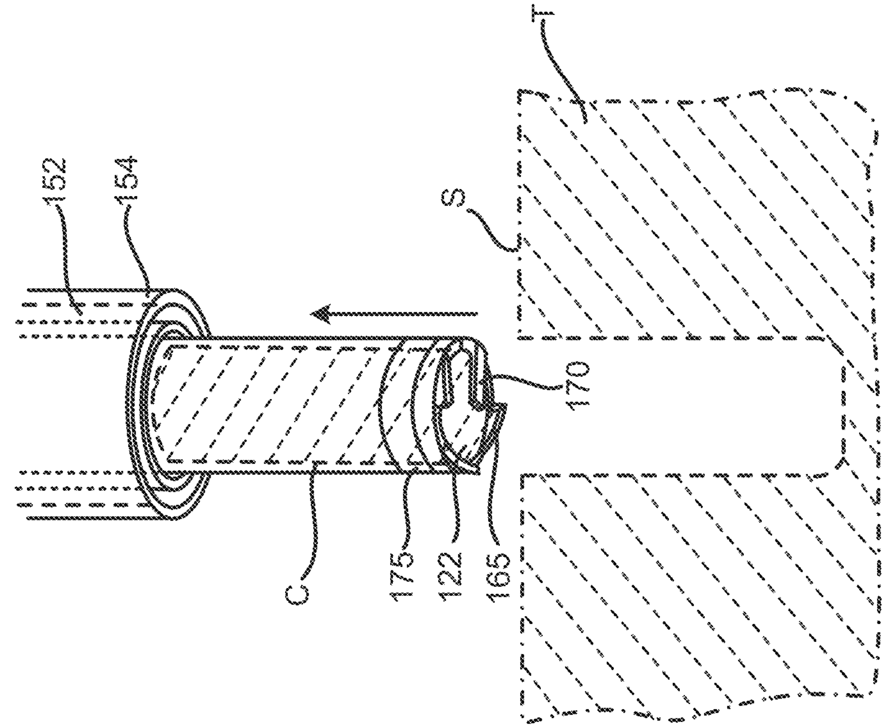
FIG. 4D is a schematic view of another step of the method of use wherein the cutting sleeve is withdrawn from the targeted tissue with a tissue core captured in the lumen of the cutting sleeve.

Now turning to FIGS. 4A to 4D, a method of using the RF device 100 of FIGS. 1-3B is shown cutting of a tissue core C from targeted tissue T, which is then captured in lumen 122 of the cutting sleeve 115. FIG. 4A first illustrates the operator placing the distal end 154 of the introducer sleeve assembly 114 against the targeted tissue T and actuating the negative pressure source 135, thereby applying suction through the annular space 152 between the outer sleeve 145 and guide sleeve 148 to stabilize and couple the tissue surface S to the sleeve assembly 114. FIG. 4B illustrates a subsequent step wherein the operator or controller 140 energizes the active electrode 165 to cut tissue and helically advances the cutting sleeve 115 into tissue, which captures a tissue core C in the lumen 122 of the cutting sleeve. FIG. 4C illustrates a subsequent step where the cutting sleeve is extended distally to the end of its helical stroke, and the operator or controller 140 rotates the cutting sleeve 115 at least 360° to excise a distal end 182 of the tissue core C thereby mobilizing the core for removal from the patient's body. FIG. 4D illustrates the withdrawal of the cutting sleeve 115 from the targeted tissue T by retracting the entire device 100. In another variation, the motor drive 120 may be operated to retract the cutting sleeve 115 into the guide sleeve 148 either helically or axially. In another variation of a method of operation, the above steps shown in FIGS. 4A-4C can be repeated to capture and stack or plurality of tissue cores C in lumen 122 of the cutting sleeve 115. Following withdrawal of the cutting sleeve 115 from the targeted tissue T, the tissue cores C may be retrieved from the lumen 122 in the cutting sleeve by detaching the shaft component 110 from the handle 106 as shown in FIG. 2 and using a pushrod (not shown) to expel the captured tissue core C or cores from the cutting sleeve 115. The stroke of a cutting sleeve can be from 2 mm to 20 mm with 2 to 20 helical revolutions.

Figure 5A:
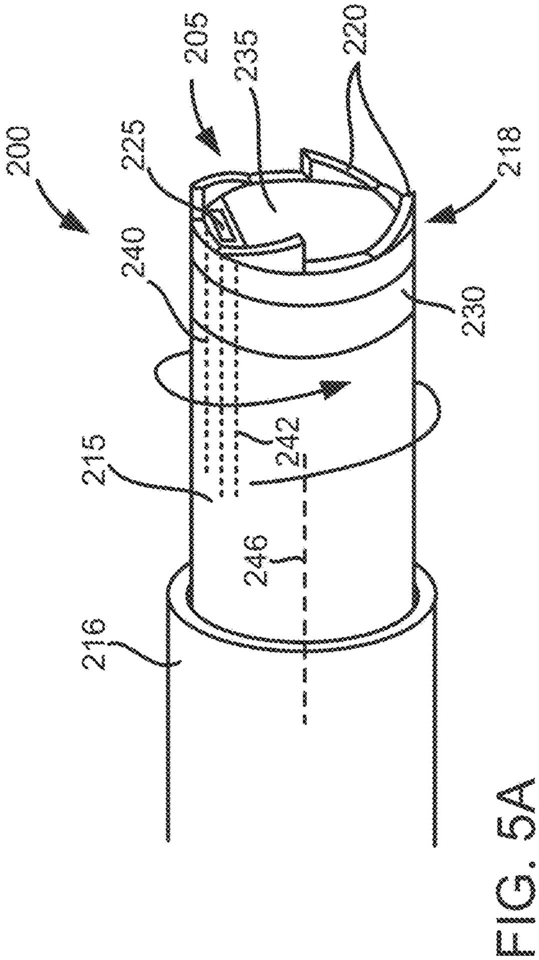
FIG. 5A illustrates a working end of another variation of an RF device with outer sleeve assembly comprising a guide sleeve and a co-axial inner cutting sleeve that carries and extendable-retractable active projecting electrode, with the projecting electrode in a retracted position.
Figure 5B:
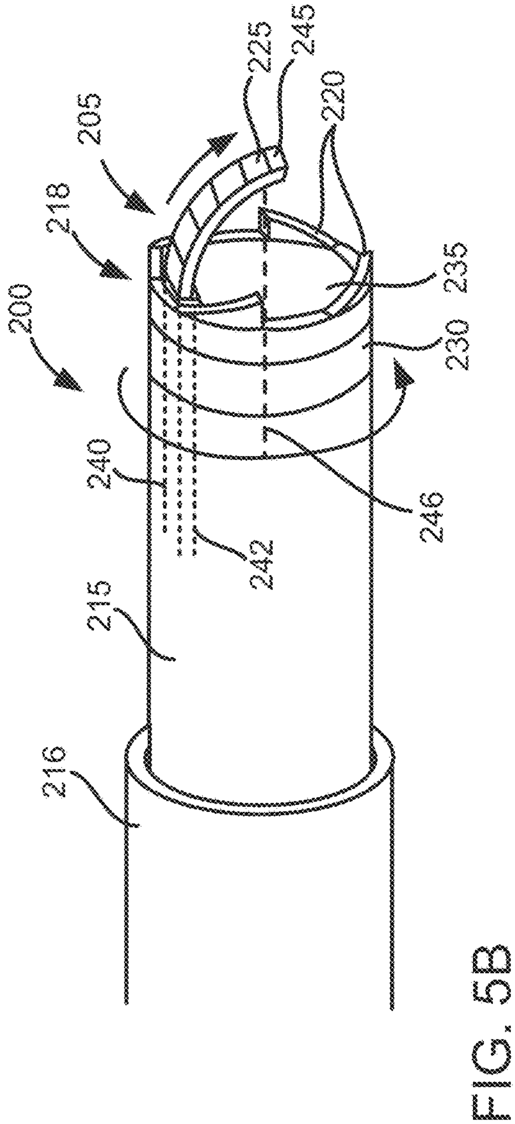
FIG. 5B illustrates the working end of FIG. 5A with the projecting active electrode in an extended position, which is angled to cross the central axis of the lumen in the cutting sleeve.

Now, turning to FIGS. 5A and 5B, the distal end of another variation of shaft assembly 200 and RF electrode arrangement 205 is shown. In this variation, the cutting sleeve 215 is helically extendable from a guide sleeve 216 as described in the variation or FIGS. 3A-3B. However, in FIG. 5A, it can be seen that the guide sleeve 216 is not surrounded by an aspiration channel for stabilizing tissue. In using the variation of FIGS. 5A-5B, an independent instrument such as a grasper is used to stabilize the targeted tissue before advancing the cutting sleeve into such tissue.

As can be seen in FIGS. 5A-5B, the distal end 218 of the cutting sleeve 215 differs from the embodiment of FIGS. 3A-3B in that the active electrode comprises two components: (i) the peripheral edge electrode 220 at the distal edge of cutting sleeve 215 and (ii) a projecting active electrode element 225 that is extendable and retractable from the distal end 218 of the cutting sleeve (FIG. 5B). The active electrode 220 of peripheral edge 222 is similar to the variation of FIGS. 3A-3B. As described above, the return electrode can comprise a ground pad in a non-saline immersed procedure, and a return electrode can comprise an annular band 230 or the interior surface of lumen 235 at the distal end 218 of the cutting sleeve 215, which will contact tissue as the cutting sleeve is advanced helically into tissue. In FIG. 5B, the elongated shaft 240 of the projecting electrode element 225 is shown fully extended from a channel 242 in the wall of the cutting sleeve 215, wherein the projecting electrode element 225 comprises a flexible member that, when extended, moves to a repose shape wherein the electrode tip 245 extends to, or across, the central axis 246 of the lumen 235 of the cutting sleeve 215. In use, the variation of FIGS. 5A-5B would function as described in the previous variation of FIGS. 3A-3B.

Figure 6:
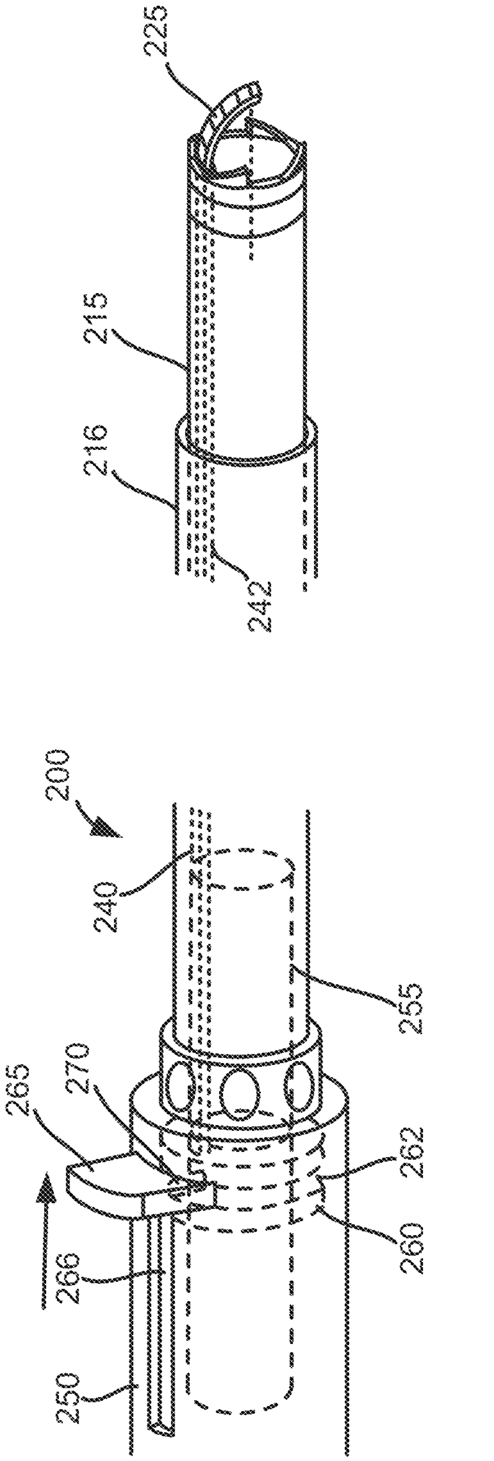
FIG. 6 is an illustration of a handle and shaft portion of the RF device of FIGS. 5A-5B showing a manually operated slider mechanism for extending and retracting the projecting electrode.

FIG. 6 schematically illustrates a handle component 250 coupled to the shaft assembly 200 of FIGS. 5A-5B, wherein the handle carries a mechanism adapted for manually extending and retracting the projecting active electrode element 225. Variations of the device shown in FIG. 6 can include coatings on the sleeve 215 as described above. As also described above, the motor drive (cf. FIGS. 1 and 2) is operatively coupled to a drive sleeve 255 and is configured to helically advance the drive sleeve in the distal direction. The drive sleeve 255 is coupled to the cutting sleeve 215, as described in previous variations. In this variation, a flange 260 or collar around the drive sleeve 255 is connected to the shaft 240 of the active projecting electrode 225. The flange 260 has an annular groove 262 extending in 360° around the flange 260. A sliding grip 265 is adapted to slide in an elongated slot 266 in the handle 250 and is adapted to extend and retract the electrode shaft 240 relative to the cutting sleeve 215. As can be seen in FIG. 6, the sliding grip 265 has a radially inward projecting pin 270 that is received by the annular groove 262 in flange 260. Thus, it can be understood that as the drive sleeve 255 helically advances the cutting sleeve 215, the sliding grip 265 will move in the elongated slot 266. When the cutting sleeve 215 reaches the distal end of its helical stroke, the operator can then move the sliding grip 265 distally to extend the projecting active electrode element 225 outwardly from channel 242 in the cutting sleeve 215, as is shown in FIG. 6. Thereafter, the motor drive can be used to rotate the cutting sleeve 215, and the projecting active electrode element 225 will excise the distal end of the tissue core captured in the lumen of the cutting sleeve. Following mobilization of a captured tissue core as described above, the sliding grip 265 can be moved proximally to retract the projecting electrode back 225 into channel 242 to prepare for cutting additional tissue cores.

Figure 7A:
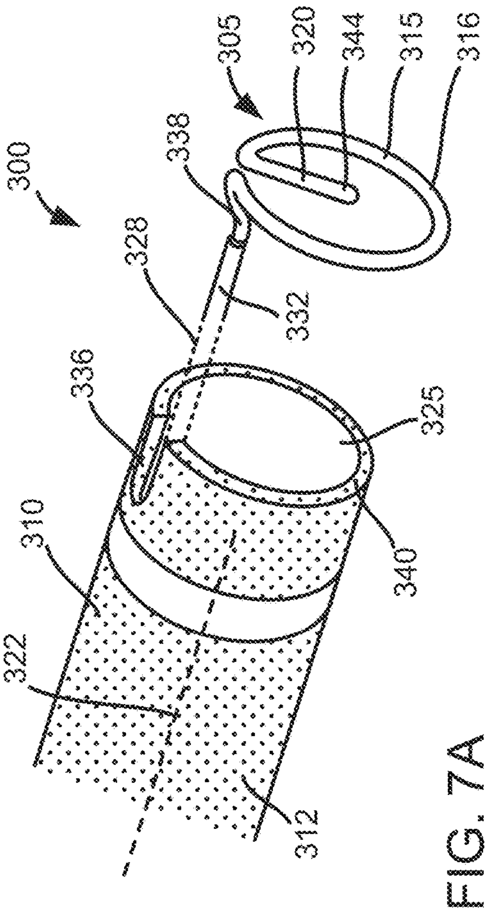
FIG. 7A illustrates an exploded view of a distal end of a cutting sleeve of another variation of RF, where such a cutting sleeve can be helically advanced from a guide sleeve (not shown) as in the variation of FIGS. 5A-5B, with the electrode arrangement in part comprises a wire formed into a circular form with projecting element that projects inwardly to the central axis of the lumen in the cutting sleeve.
Figure 7B:
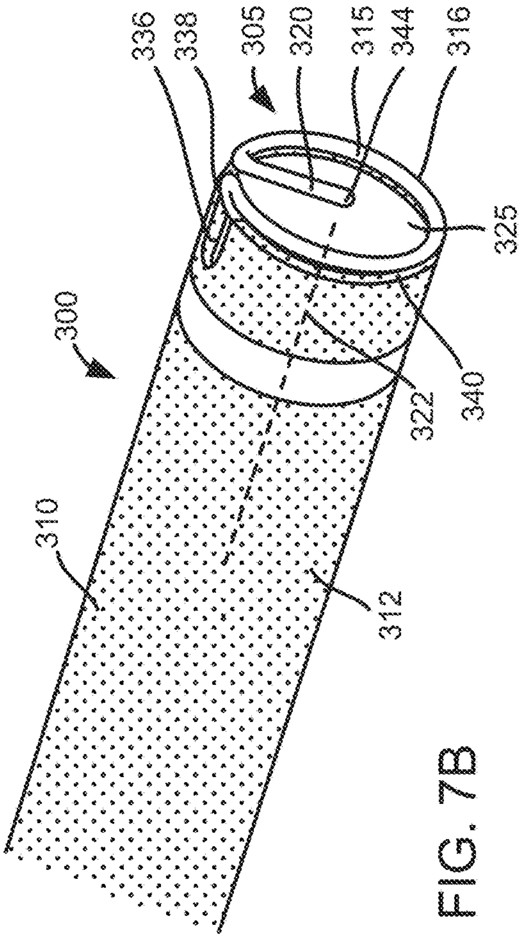
FIG. 7B illustrates the cutting sleeve and electrode arrangement of FIG. 7A in assembled configuration.
Figure 8:
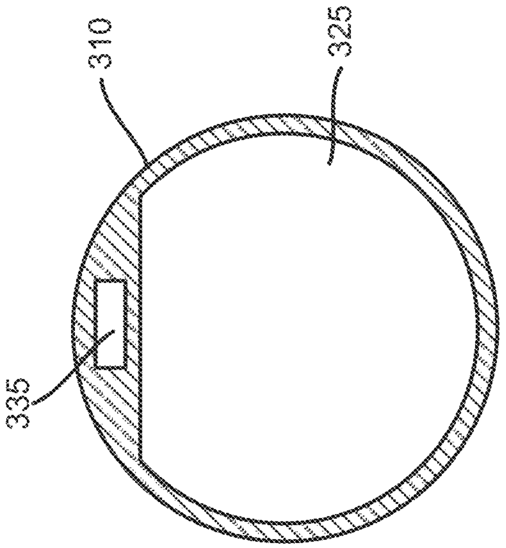
FIG. 8 is a cross-section of a variation of a cutting sleeve as in FIGS. 7A-7B with a rectangular channel therein for carrying a rectangular electrode shaft of an active electrode as in FIGS. 7A-7B.

FIGS. 7A and 7B illustrate the distal end of another variation of a cutting sleeve 300 and RF electrode arrangement 305. In this variation, the cutting sleeve 300 is helically extendable from a guide sleeve (not shown) of the type described above in the variation of FIGS. 5A-5B. In FIGS. 7A-7B, it can be the cutting sleeve 300, again comprised a thin-wall tubular member 310 with an insulative coating 312 that is coupled to a different form of active electrode 315. The active electrode 315 comprises a wire that is formed into a distal circular shaped portion 316 with a projecting electrode element 320 that projects radially inward across the central axis 322 of the lumen 325 of the cutting sleeve 300 to operate as described in the previous variations of FIGS. 3A-3B and FIGS. 5A-5B. FIG. 7A is an exploded view of the components, which shows the active electrode 315 separated from the tubular member 310 of the cutting sleeve. An elongate shaft portion 328 of the active electrode 315 has an insulative sheath 332 and may be secured in, or against, the wall of the tubular member 310 by suitable means such as a receiving channel 335 shown in FIG. 8 which is a cross-sectional view of the tubular member 310. In FIGS. 7A-7B, the distal end of the tubular member 310 is shown with an axial slot 336 for receiving an outward bend 338 of the shaft portion 328 of the active electrode 315. As can be seen in FIG. 7B, the circular-shaped portion 316 of the active electrode 315 is positioned in close proximity to the distal edge 340 of the tubular member 310. In order to prevent rotation of the circular-shaped portion 316 of active electrode 315 relative to the tubular member 310, a non-round channel 335, as in FIG. 8, can receive the shaft portion 328 of electrode 315 that has a polygonal shape, such as a rectangular shaft.

Referring to FIG. 7B, it can be seen that the projecting element 320 of the active electrode 315 projects inwardly in a plane that is transverse to the central axis 322 of the cutting sleeve 300. However, it should be appreciated that the projecting electrode element 320 can extend distally from such a transverse plane and may be angled in the distal direction or otherwise have a curve shape with the distal tip 344 of such a projecting electrode element 320 extending from the periphery to, or across, the central axis 322 to again perform the method of the invention as described above. All the considerations of return electrode placement and orientation described above apply to this variation of the cutting sleeve 310 and a guide sleeve.

Figure 9:
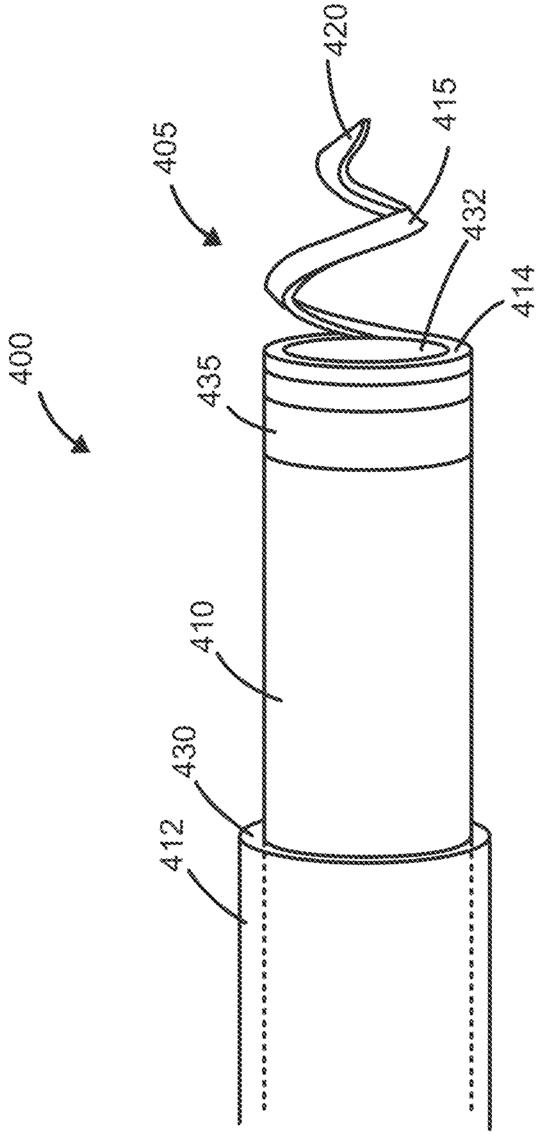
FIG. 9 illustrates another variation of a guide sleeve and a helically advanced cutting sleeve wherein the active electrode extends around a distal edge of the cutting sleeve and has a projecting element in a helical form that tapers in the distal direction to a tip that crossed the central axis of the lumen in the cutting sleeve.

FIG. 9 illustrates the distal end of another variation of shaft assembly 400 and RF electrode arrangement 405, where the sleeve 410 can have a coating as described above. In this variation, the cutting sleeve 410 again is helically extendable from a guide sleeve 412 as described above relating to the variation of FIGS. 5A-5B. In FIG. 9, it can be seen that the active electrode 405 extends around a distal periphery 414 of the cutting sleeve 410 and includes an active electrode extending element 415 that has a helical configuration that tapers in the distal direction to a distal-most tip 420. Thus, the variation of FIG. 9 provides a helical electrode extending element 415 that can function as a screw to assist in driving the cutting sleeve 410 into targeted tissue. This screw-like effect can reduce or eliminate the need to stabilize the targeted tissue while driving the cutting sleeve 410 into tissue. In this variation, the return electrode again can comprise the distal tip 432 of the guide sleeve 412 initially is using the device, and another return electrode 435 is shown on the exterior of cutting sleeve 410, but all the considerations of return electrode arrangements described above apply to this variation.

As can be understood from FIG. 9, after the helical active electrode element 415 and cutting sleeve 410 are helically advanced into targeted tissue, then rotating the cutting sleeve 410 without helical movement will excise the distal end of a tissue core captured in the lumen 432 of the cutting sleeve 410 as described in earlier variations. In a variation, the drive mechanism in a handle (cf. FIGS. 1 and 2) can be configured to helically drive the cutting sleeve 410 and helical electrode element 415 at a pitch that approximately corresponds to the pitch the helical electrode element 415.

Figure 10:
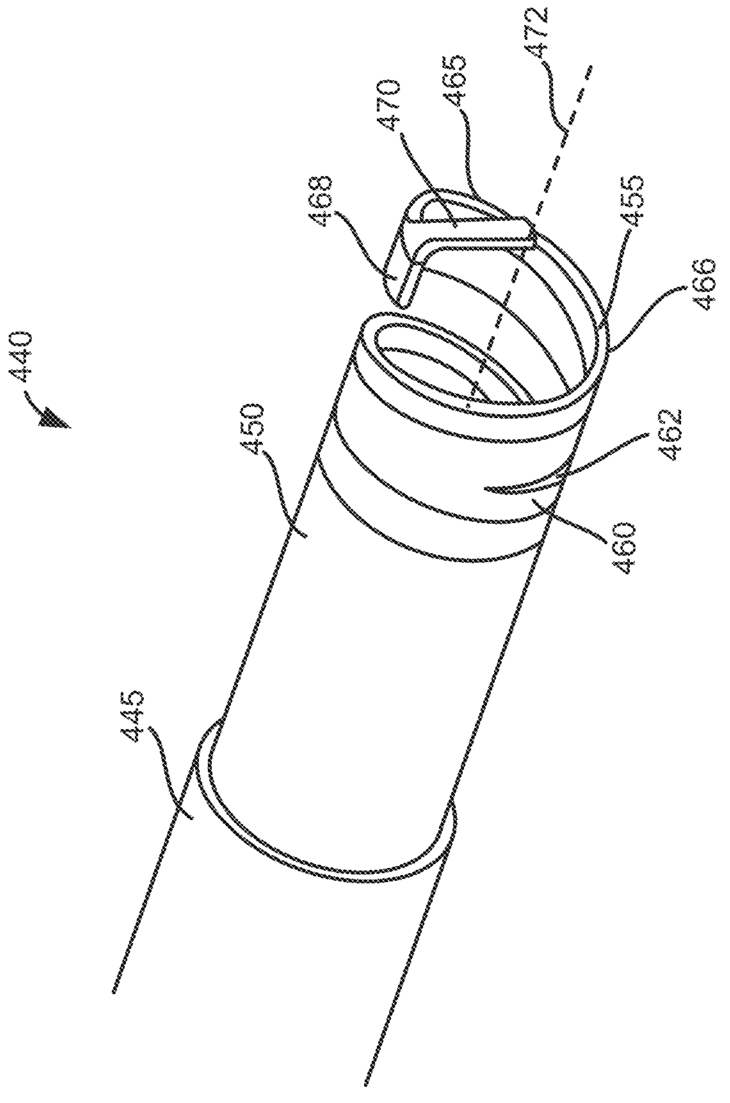
FIG. 10 illustrates another variation of a guide sleeve and a helically advanced cutting sleeve wherein the distal end of the sleeve wall has a helical form carrying an active electrode at its distal edge and a distal projecting electrode element that projects inwardly to cross the central axis of the lumen in the cutting sleeve.

Now, turning to FIG. 10, another variation of a distal end of an RF device 440 is shown with a guide sleeve 445, cutting sleeve 450, and RF active electrode 455. Again, variations of the device can include a coating on the sleeve 450 as described above. In this variation, the cutting sleeve 450 again is helically extendable from a guide sleeve 445, as described in previous variations. In the variation of FIG. 10, the distal end 460 of the thin-wall cutting sleeve 450 has a wall 462 that transitions into to a helical member 465 that carries the active electrode 455 at its distal edge 466. At the distal end 468 of the helical member 465, a projecting active electrode element 470 projects inward from the periphery to the central axis 472, as in earlier variations. The helical member 465 can extend at least 180° around the central axis 472 and more often extend from 360° to 720° relative to the central axis 472. The helical member 465 again is adapted to assist in pulling the cutting sleeve 450 into targeted tissue to reduce or eliminate the need for a tissue stabilization mechanism. All the considerations of return electrode placement and orientation described above apply to this variation of a shaft assembly of an RF device. In a method of use, the variation of FIG. 10 would be the same as described above, with helical advancement in tissue to cut a tissue core followed by rotation of the cutting sleeve to excise the distal end of the tissue core captured in the lumen of the cutting sleeve.

Although particular variations of the present invention have been described above in detail, it will be understood that this description is merely for purposes of illustration, and the above description of the invention is not exhaustive. The variations above are shown with a motor drive for moving a cutting sleeve helically and rotationally, but manually operated mechanisms are also possible for either or both such helical and rotational movements. Specific features of the invention are shown in some drawings and not in others, and this is for convenience only, and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Various changes may be made to the invention described, and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

The invention claimed is:

1. A method of obtaining a tissue core for biopsy:

providing an elongate cutting member having a longitudinal passageway extending about a central axis to a distal end carrying a radio frequency (RF) electrode, wherein at least a portion of the RF electrode extends from an outer periphery of the elongate cutting member to the central axis; and actuating the RF electrode;

helically advancing the elongate cutting member into a targeted tissue region wherein the RF electrode cuts tissue to thereby capture a tissue core in the longitudinal passageway;

rotating the elongate cutting member without helical advancement thereby causing the RF electrode to cut a distal end of the tissue core captured in the longitudinal passageway; and withdrawing the elongate cutting member from the targeted tissue region thereby obtaining an extracted tissue core.

2. The method of claim 1 including actuating the RF electrode contemporaneous with helically advancing the elongate cutting member into the targeted tissue region.

3. The method of claim 1 wherein helically advancing and rotating the elongate cutting member are accomplished with a drive mechanism in a handle coupled to the elongate cutting member.

4. The method of claim 3 wherein the drive mechanism comprises a motor drive.

5. The method of claim 3 wherein the drive mechanism comprises a manually actuated mechanism.

6. The method of claim 3 wherein helically advancing the elongate cutting member is accomplished with a first drive mechanism and rotating the elongate cutting member is accomplished with a second different drive mechanism.

7. The method of claim 3 wherein the elongate cutting member is helically advanced from an outer sleeve coupled to the handle.

8. The method of claim 7 further comprising stabilizing the targeted tissue region contemporaneous with helically advancing the elongate cutting member.

9. The method of claim 8 wherein stabilizing is accomplished by at least one of coupling the distal end of the outer sleeve with a surface of the tissue with negative pressure in the outer sleeve or grasping the surface of the targeted tissue region with a grasping device.

10. The method of claim 8 wherein the distal end of the elongate cutting member is configured with a helical element that helically drives the elongate cutting member into tissue which stabilizes the targeted tissue region.

11. The method of claim 1 further comprising obtaining multiple tissue cores by repeating actuating, helically advancing and rotating the elongate cutting member to obtain each additional tissue core.

12. The method of claim 1 wherein the elongate cutting member and longitudinal passageway are configured to obtain a tissue core having a diameter ranging from 1 mm to 15 mm.

13. The method of claim 1 wherein the elongate cutting member and longitudinal passageway are configured to obtain a tissue core having a length ranging from 2 mm to 20 mm.

14. An electrosurgical tissue cutting device for obtaining a tissue core for biopsy:

a handle coupled to an elongate shaft assembly extending about a central axis and comprising an outer sleeve and an inner cutting sleeve coaxial to the outer sleeve and with a longitudinal passageway therein for capturing tissue;

a radio frequency (RF) electrode carried at a distal end of the inner cutting sleeve, wherein an extending element of the RF electrode extends from an outer periphery of the inner cutting sleeve to the central axis; and at least one selectable drive mechanism in the handle for (i) helically advancing the inner cutting sleeve distally from the outer sleeve, and for (ii) rotating the inner cutting sleeve in the outer sleeve without helical advancement.

15. The electrosurgical tissue cutting device of claim 14 further comprising a negative pressure source coupled to the elongate shaft assembly.

16. The electrosurgical tissue cutting device of claim 15 wherein the negative pressure source communicates with an annular passageway in the outer sleeve outward of the inner cutting sleeve for stabilizing targeted tissue region.

17. The electrosurgical tissue cutting device of claim 15 wherein the negative pressure source communicates with the longitudinal passageway in the inner cutting sleeve for aspirating cut tissue therein.

18. The electrosurgical tissue cutting device of claim 15 wherein a drive mechanism comprises a motor drive.

19. The electrosurgical tissue cutting device of claim 14 wherein a drive mechanism comprises a manually actuated mechanism.

20. The electrosurgical tissue cutting device of claim 18 further comprising an RF source coupled to the RF electrode and a controller adapted to control the RF source, the negative pressure source and at least one selectable drive mechanism.

21. The electrosurgical tissue cutting device of claim 14 further comprising a detachable coupling between the handle and the elongate shaft assembly for detaching at least a portion of the elongate shaft assembly for retrieval of tissue cores from the inner cutting sleeve.

22. The electrosurgical tissue cutting device of claim 14 wherein a distal edge of the inner cutting sleeve around the longitudinal passageway comprises an RF electrode.

23. The electrosurgical tissue cutting device of claim 14 wherein the extending element of the RF electrode that extends from the outer periphery of the inner cutting sleeve toward the central axis has a non-helical configuration.

24. The electrosurgical tissue cutting device of claim 14 wherein the extending element of the RF electrode that extends from the outer periphery of the inner cutting sleeve toward the central axis has a helical configuration.

25. The electrosurgical tissue cutting device of claim 24 wherein the extending element of the RF electrode with the helical configuration extends helically at least 360° about the central axis.

26. The electrosurgical tissue cutting device of claim 14 wherein the extending element of the RF electrode that extends from the outer periphery of the inner cutting sleeve toward the central axis is extendable and retractable.

* * * * *